(12) United States Patent
Martin, IV

(10) Patent No.: US 12,315,603 B2
(45) Date of Patent: May 27, 2025

(54) MEDICAL PROCEDURE DOCUMENTATION SYSTEM AND METHOD

(71) Applicant: Charles Martin, IV, Pepper Pike, OH (US)

(72) Inventor: Charles Martin, IV, Pepper Pike, OH (US)

(*) Notice: Subject to any disclaimer, the term of this patent is extended or adjusted under 35 U.S.C. 154(b) by 321 days.

(21) Appl. No.: 17/939,341

(22) Filed: Sep. 7, 2022

(65) Prior Publication Data

US 2023/0073975 A1 Mar. 9, 2023

Related U.S. Application Data

(60) Provisional application No. 63/241,204, filed on Sep. 7, 2021.

(51) Int. Cl.
*G16H 10/60* (2018.01)
*G06F 3/16* (2006.01)
*G10L 15/26* (2006.01)
*H04N 5/77* (2006.01)
*H04N 7/18* (2006.01)
*H04N 23/66* (2023.01)

(52) U.S. Cl.
CPC ............ *G16H 10/60* (2018.01); *G06F 3/165* (2013.01); *G10L 15/26* (2013.01); *H04N 5/77* (2013.01); *H04N 7/183* (2013.01); *H04N 23/66* (2023.01)

(58) Field of Classification Search
CPC .......... G06F 3/165; H04N 5/77; H04N 7/183; H04N 23/66; H04N 23/60; G16H 15/00; G16H 30/20
See application file for complete search history.

(56) References Cited

U.S. PATENT DOCUMENTS

| | | |
|---|---|---|
| 6,031,526 A | 2/2000 | Shipp |
| 6,102,505 A | 8/2000 | McIntyre et al. |
| 8,313,432 B2 | 11/2012 | Chiu et al. |
| 9,412,361 B1 | 8/2016 | Geramifard et al. |
| 10,740,552 B2 | 8/2020 | Hanning |
| 10,957,427 B2 | 3/2021 | Owen et al. |
| 2002/0143533 A1 | 10/2002 | Lucas et al. |
| 2007/0294105 A1* | 12/2007 | Pierce .................... G16H 40/67 600/300 |
| 2022/0310113 A1* | 9/2022 | Tzinis .................... G06V 10/82 |

OTHER PUBLICATIONS

Written Opinion of the International Searching Authority dated Dec. 28, 2022.

* cited by examiner

*Primary Examiner* — Nicholas G Giles

(74) *Attorney, Agent, or Firm* — Jacob M. Ward; Ward Law Office LLC

(57) ABSTRACT

The present invention relates to a system and method for documenting medical procedures. The system can include an audio recording system and an image recording system. An actuator can be configured to actuate each of the audio recording system and the image recording system, wherein the audio recording system is configured to be actuated after the image recording system. A control system can be configured to receive input from each of the audio recording system and image recording system.

15 Claims, 4 Drawing Sheets

MEDICAL PROCEDURE DOCUMENTATION SYSTEM AND METHOD

CROSS-REFERENCE TO RELATED APPLICATIONS

This application claims the benefit of U.S. Provisional Application No. 63/241,204, filed on Sep. 7, 2021. The entire disclosure of the above application is incorporated herein by reference.

FIELD

The present technology relates to a documentation system and, more specifically, to a medical documentation system.

INTRODUCTION

This section provides background information related to the present disclosure which is not necessarily prior art.

The healthcare industry is a complicated, highly regulated industry that provides a product for serving every type of human condition in every combination possible. As such, detailed documentation of patient diagnosis, conditions, treatments, procedures, and the frequency and time of each is mandatory.

Contrary to general belief, a hospital is not paid based on what the detailed bill indicates. Hospitals are generally paid on a Diagnostic Related Group (DRG), which is based on the patient's diagnosis that was the primary reason for admission to the hospital, complications involved with the patient's condition and/or during the patient's hospitalization, and procedures performed during the hospitalization. Each different DRG (there are over 500) provides for different reimbursement. Furthermore, within a "grouping," there are different sub-categories of reimbursement that are driven by the complications and treatment of those complications.

What is more, insurers may require additional support for medical procedures and charges documented on the patient's bill. Some of those procedures may even require supplemental supporting documentation to corroborate the medical procedures and charges. These extra recording steps and documents can further complicate reimbursement of patient care.

Currently, a physician will perform a procedure without performing any documentation. After the procedure, the physician may then dictate notes from the procedure. This process can be time consuming and may lead to a loss of detail in the report that is only available with contemporaneous documentation.

Accordingly, there is a need for a medical procedure documentation system, which allows for documentation to be collected during a medical procedure.

SUMMARY

In concordance with the instant disclosure, a medical procedure documentation system, which allows for documentation to be collected during a medical procedure, has surprisingly been discovered.

In certain embodiments, a medical procedure documentation system for capturing audio and images is provided. The system can include an audio recording system, an image recoding system, an actuator, and a control system. The actuator can be configured to actuate each of the audio recording system and the image recording system. The audio recording system can be configured to be actuated after the image recording system. The control system can be configured to receive input from each of the audio recording system and the image recording system.

In certain embodiments, a method for documenting a medical procedure is provided. A medical documentation system as described herein can be provided. The medical documentation system can include an audio recording system, image recording system, an actuator, and a control system. A medical procedure can be performed. The actuator can be depressed to engage the image recording system to create an image. The actuator can be released to engage the audio recording system. The medical procedure information can be dictated to the audio recording system to create procedural notes. The audio recording system can be signaled to end the recording. The audio recording system can be signaled by either a spoken word or by an additional further physical actuation. The control system can process and align the image and the procedural notes.

In certain embodiments, the present disclosure relates to a system for documenting a medical procedure by an operator. The system can include an audio recording system, an image recording system, an actuator, and a control system. The system can allow the operator to dictate notes during the medical procedure, which can later be coupled with still images recorded by the image recording system. These temporally aligned notes and images can then be used for medical documentation purposes, such as billing.

The audio recording system can include a microphone. In certain embodiments, the microphone can be worn by the operator. The recording system can be configured to record dictated notes from the operator. The notes can include dictations regarding various types of information, including information collected or related to triage, pathology, treatment, and/or testing, as based on what the operator is experiencing as well as visualizing during the procedure. The notes can also include descriptions of treatments or interventions performed during a procedure.

The image recording system can record one or more portions of the medical procedure, such as recording a fluoroscopic segment or run, depending on the type of procedure. The image recording system can include a video camera for certain surgical applications. The image recording system can include a camera or endoscope, for certain embodiments.

Each of the audio recording system and the image recording system can be actuated by the actuator. The actuator can be a physical actuator such as a foot pedal or a button in the operating room. Where the actuator is a foot pedal, in particular, the image recording system can record or otherwise capture a still image immediately upon a depression of the pedal. The audio recording system can be actuated upon a release of the pedal. Accordingly, the image can be captured first and the operator can then dictate relevant notes immediately upon capturing the image. The recording system can then be deactivated by either a spoken word or an additional further physical actuation.

It should be appreciated that actuation of the audio recording system, which can function as a "reverse dead man switch," can promote privacy of a patient undergoing a procedure. The system of the present disclosure does not rely on ambient listening to actuate the system. Such ambient listening systems can capture patient information that was not meant to be recorded. Alternatively, the present system allows the operator to start capturing one or more images, while providing a stop gap before the dictated notes are recorded. This allows the operator to minimize any unnecessary recordings.

Additionally, the system allows the operator to record dictated notes contemporaneously with the performed medical procedure. This allows for more accurate notes while also eliminating additional documentation steps the operator typically performs after the procedure is complete.

The recorded images from the image recording system and the dictated notes recorded by the audio recording system can be processed by the control system. The control system can be configured to decouple or otherwise separate the recorded audio and the recorded images during processing, while also appropriately associating the recorded audio with images so the data can be temporally aligned or correlated.

The control system can be configured to translate the spoken audio into text. The control system can also be configured to produce still images from the captured images where video was recorded. The control system can associate the still images and the written text such that the written text is temporally aligned with the still image related to the written text as dictated during the procedure. As a non-limiting example, the control system can utilize a machine learning process to associate related text with related images. In certain embodiments, the control system can also label particular procedures or runs, for example fluoroscopic runs performed by a radiologist, which can reduce the need for technologist intervention during the procedure.

In operation of the medical procedure documentation system, the operator can perform the medical procedure. During the medical procedure, the operator can depress the foot pedal to capture an image. The operator can release the pedal and then dictate the necessary notes. The operator can then signal the audio recording system to stop recording. These steps can be repeated as necessary through the duration of the procedure. The control system can then process the inputs as described herein.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Figure 1:
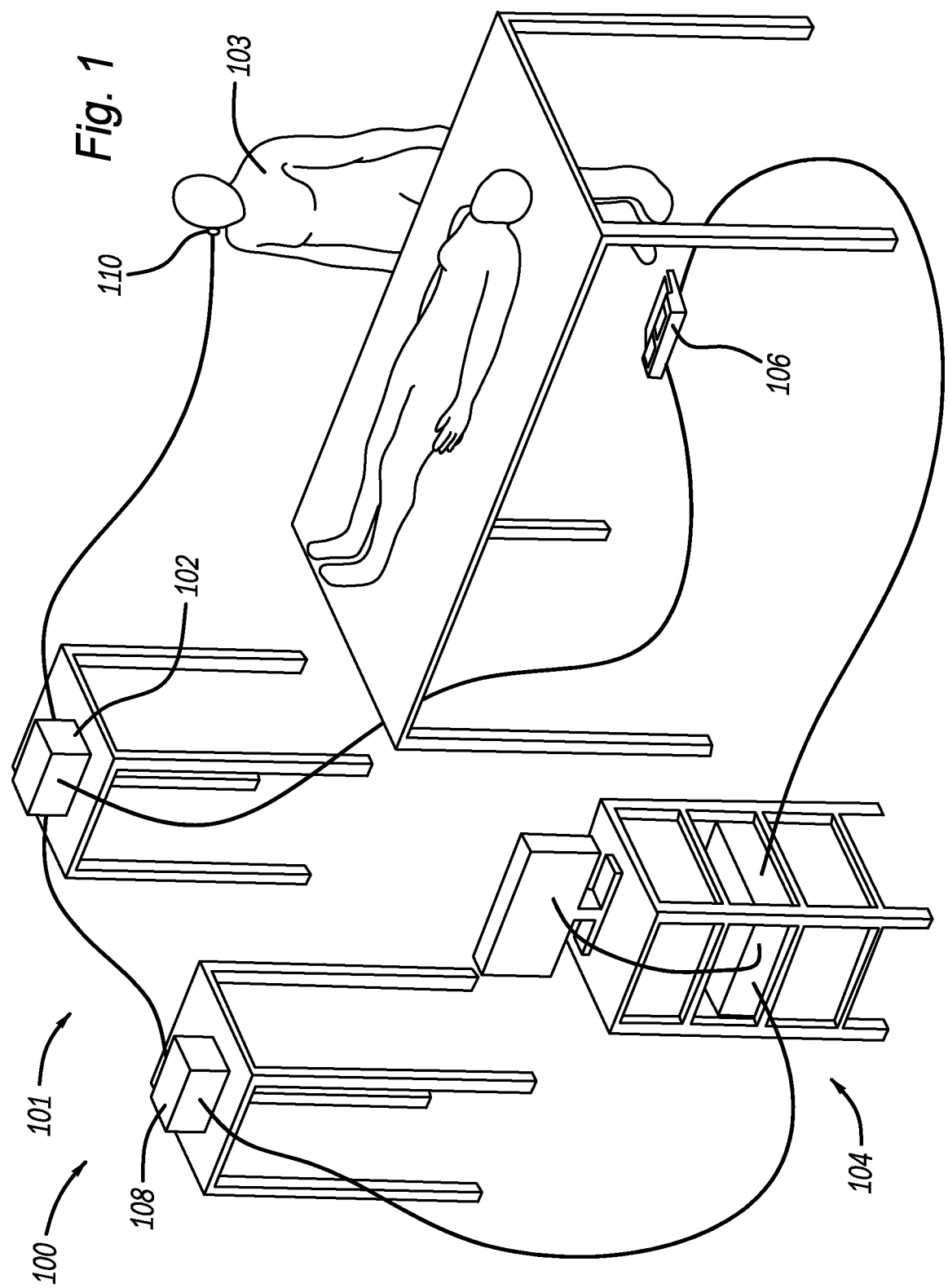
FIG. 1 is a top perspective view of a medical procedure documentation system shown in an operating room environment.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments, including where certain steps can be simultaneously performed, unless expressly stated otherwise. "A" and "an" as used herein indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The present technology relates to a medical procedure documentation system 100, and method 200 for documenting medical procedure information, shown generally in the accompanying figures.

Figure 2:
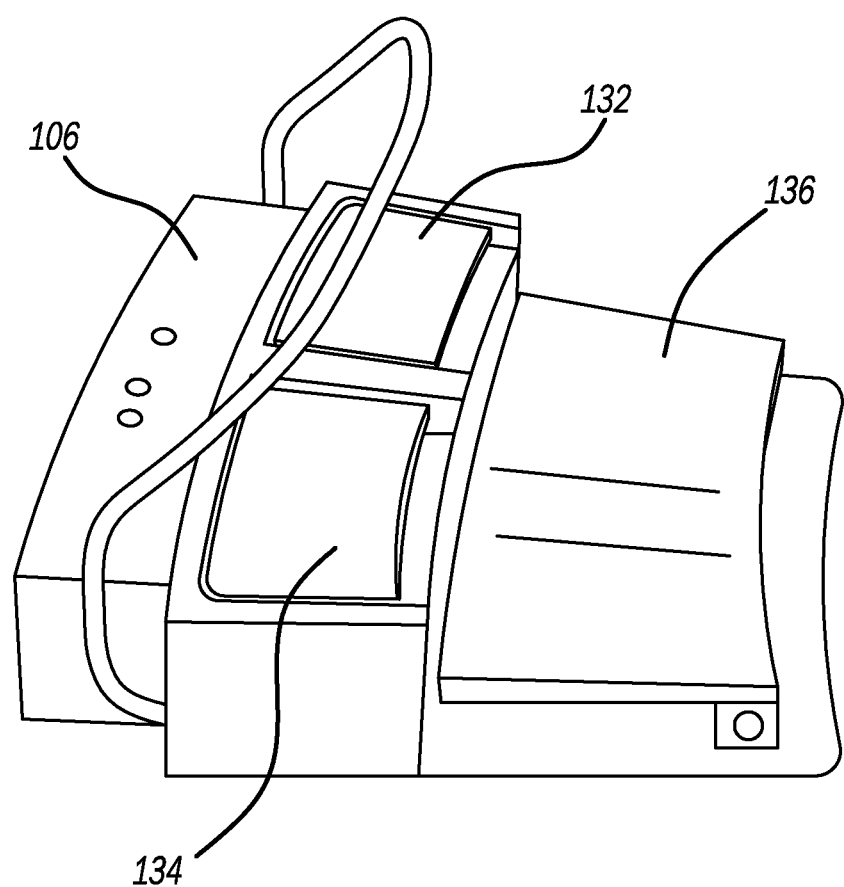
FIG. 2 is a top perspective view of an actuator of the medical procedure documentation system.
Figure 3:
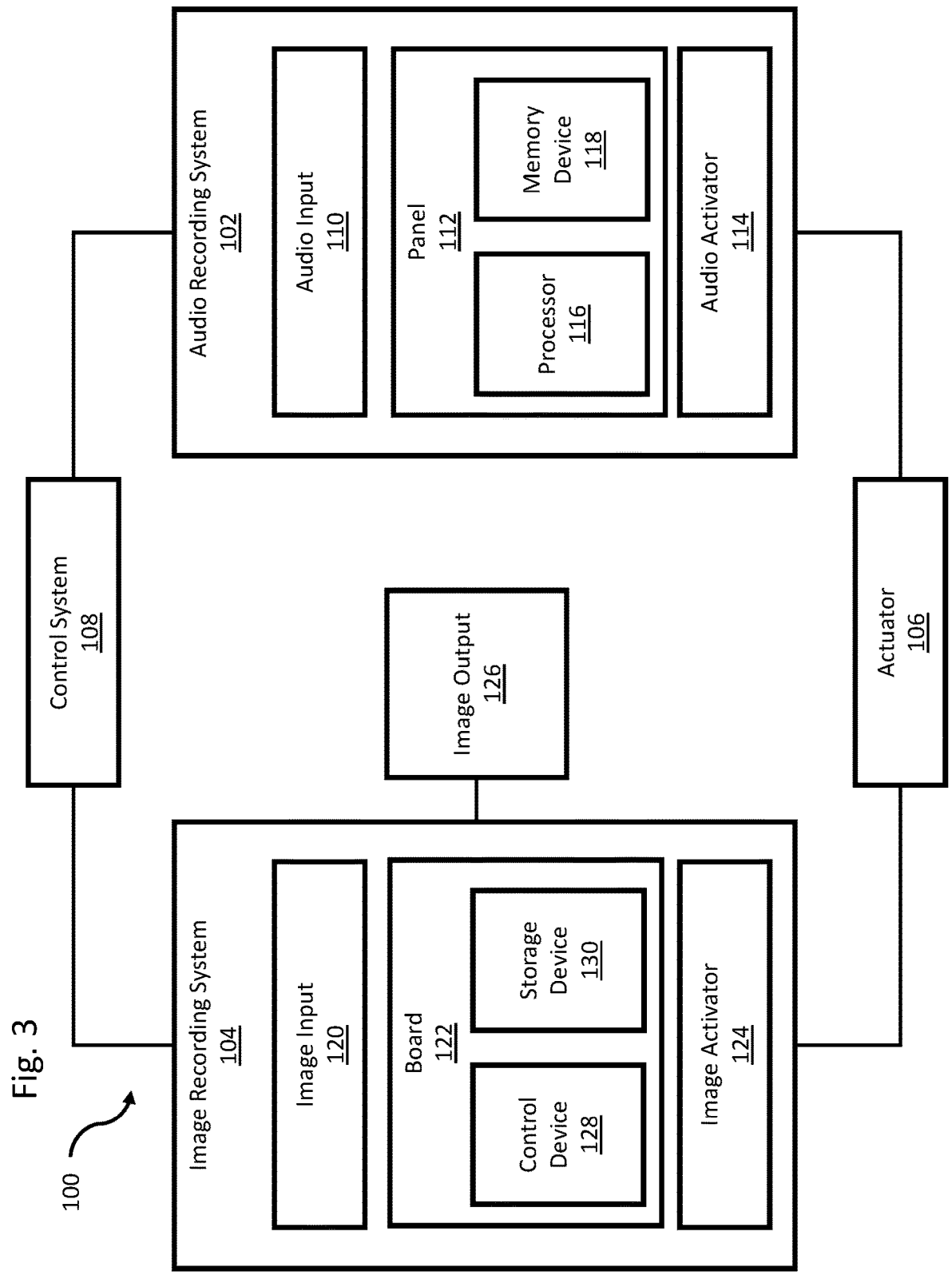
FIG. 3 is a schematic view of the medical procedure documentation system.

As shown in FIGS. 1-3, the documentation system 100 can include an audio recording system 102, an image recording system 104, an actuator 106, and a control system 108. The system 100 can be used in any type of medical environment. As a non-limiting example, the system 100 can be used during a procedure in an operating room 101. The system 100 can be configured such that the actuator 106 can individually control the audio recording system 102 and the image recording system 104. The audio recording system 102 and the image recording system 104 can then relay the audio and image collected to the control system 108 which, in turn, can couple and temporally align the audio with the image.

The audio recording system 102 can be configured to record audio from an operator 103. The audio can include dictations regarding various types of information. More specifically, the information can include information collected or related to triage, pathology, treatment, and/or testing, as based on what the operator 103 is experiencing as well as visualizing during the procedure. The audio can also include descriptions of treatments or interventions performed during a procedure. With reference to FIG. 3, the audio recording system 102 can include an audio input 110, a panel 112, and an audio activator 114.

With reference to FIG. 1, the audio input 110 can be configured to receive speech of the operator 103, such as a microphone. As a non-limiting example, the microphone can be one of a handheld microphone, a lapel microphone, an embedded microphone (such as those embedded within eyeglasses, smart phones, tablet computers and/or watches) or a directional microphone array having a plurality of microphones. Advantageously, the microphone can be worn by the operator 103 to allow for hands-free operation of the documentation system 100. The microphone can also be positioned away from the operator 103 to allow for more than one individual to use the microphone at a time. Advantageously, this can allow for multiple operating room doctors, nurses, and staff to use the documentation system 100 and all contribute to the audio and therefore, documentation, for a single medical procedure. In certain embodiments, the audio recording system 102 can include a plurality of audio recording systems when a clinical environment is larger, or a higher level of resolution is desired.

As a non-limiting example, the audio input 110 can include: one or more clinical documentation client electronic devices (e.g., clinical documentation client electronic device, examples of which may include but are not limited to a handheld microphone, a lapel microphone, an embedded microphone (such as those embedded within eyeglasses, smart phones, tablet computers and/or watches) and an audio recording device). A skilled artisan can select other suitable audio inputs 110 within the scope of the present disclosure.

As shown in FIG. 3, the panel 112 can include one or more processors 116 as well as one or more memory devices 118. The processor 116 can control the overall operation of the audio recording system 102 and can include hardwired circuitry, programmable circuitry that executes software, or a combination thereof. As a non-limiting example, the processor 116 can include one or more general- or special-purpose programmable microprocessors and/or microcontrollers, application specific integrated circuits (ASICs), programmable logic devices (PLDs), programmable gate arrays (PGAs), or the like.

The memory device 118 can be configured to store audio dictated by the operator during a procedure and the audio can later be translated by the control system 108 and coupled and temporally aligned with an image recorded by an image recording system 104. As a non-limiting example, the memory device 118 can include any combination of one or more random access memories (RAMS), read-only memories (ROMs) (which may be programmable), flash memory, and/or other similar storage devices. A skilled artisan can select any combination of memory device 118 within the scope of the present disclosure.

With reference to FIGS. 1 and 3, the audio activator 114 can be coupled to the actuator 106. Upon the actuator 106 being triggered, the audio activator 114 can relay to the audio recording system 102 to begin recording and the operator 103 can begin speaking into the audio input 110. The audio recording system 102 can be deactivated by either a spoken word or by an additional further physical actuation.

The image recording system 104 can be configured to record a portion of the procedure. The image recording system 104 can also record a fluoroscopic segment or run, depending on the type of procedure. The image recording system 104 can provide the ability to capture live video and video frames as still images. With reference to FIG. XXX, the image recording system 104 can include an image input 120, a board 122, and an image activator 124.

As shown in FIG. 3, the image input 120 can be configured to record video or still images of the procedure. The image recording system 104 can receive an image or video generated by the image input 120 and provide an image output 126 in real time to a touchscreen monitor and/or an external monitor. As a non-limiting example, the image input 120 can be a camera, a video camera, or endoscope. A skilled artisan can select a suitable image input 120 within the scope of the present disclosure.

With reference to FIG. 3, the board 122 can include one or more control devices 128 as well as one or more storage devices 130. The control device 128 can control the overall operation of the image recording system 104 and can include hardwired circuitry, programmable circuitry that executes software, or a combination thereof. As a non-limiting example, the control device 128 can include one or more general- or special-purpose programmable microprocessors and/or microcontrollers, application specific integrated circuits (ASICs), programmable logic devices (PLDs), programmable gate arrays (PGAs), or the like.

The storage device 130, shown in FIG. 3, can be configured to store images taken by operator 103 during a procedure and coupled and temporally aligned by the control system 108 with an audio sample recorded by an audio recording system 102. As a non-limiting example, the storage device 130 can include any combination of one or more random access memories (RAMs), read-only memories (ROMs) (which may be programmable), flash memory, and/or other similar memory devices. A skilled artisan can select any combination of storage device 130 within the scope of the present disclosure.

With reference to FIG. 3, the image activator 124 can be coupled to the actuator 106. Upon the actuator 106 being physically triggered, the image activator 124 can relay to the image recording system 104 to begin recording. The image recording system 104 can be deactivated by an additional further physical actuation.

Each of the audio recording system 102 and the image recording system 104 can be coupled to and activated by the actuator 106. The actuator 106 can be a physical actuator as shown in FIG. 2. The actuator 106 can be configured to actuate the audio recording system 102 after the image recording system 104. Desirably, this can militate against the operator 103 recording audio before the operator 103 has determined what procedural notes are appropriate for an image that has been captured, saving both editing time and militating against re-recording.

With reference to FIG. 2, and as an example, the actuator 106 can have a first switch 132 configured to actuate the audio recording system 102 and a second switch 134 configured to actuate the image recording system 104, therefore allowing the operator 103 to have individual control over the audio recording system 102 and the image recording system 104. Advantageously, this can provide the operator 103 with more control over the audio and images recorded. Further, this can militate against the operator 103 recording audio before the operator 103 has determined what procedural notes are appropriate for an image that has been captured, saving both editing time and militating against re-recording. The actuator 106 can further include a third switch 136 configured to actuate the audio recording system 102 and the image recording system 104 simultaneously. Advantageously, actuating both systems 102, 104 at the same time can allow the operator 103 to record their real time thoughts and reactions to the procedure when necessary. As a non-limiting example, the actuator 106 can be a foot pedal, shown in FIG. 2, or a button in the operating room (not shown). A skilled artisan can select a suitable actuator within the scope of the present disclosure.

With reference to FIGS. 2-3, where the actuator 106 is a foot pedal, in particular, the image recording system 104 can record or otherwise capture a still image immediately upon a depression of the pedal, as described herein. The audio recording system 102 can be actuated upon a release of the pedal to both begin recording audio and cease recording one or more images. Accordingly, the image can be captured first, and the operator can then dictate relevant notes immediately upon capturing the image.

It should be appreciated that the actuation of the audio recording system 102 can function in a manner referred to as a "reverse dead man switch," which can promote privacy of a patient undergoing a procedure. Advantageously, the system 100 of the present disclosure does not rely on ambient listening to actuate the system 100. Undesirably, such ambient listening systems can capture patient information that was not meant to be recorded and is private to the patient. Alternatively, the present system 100 can allow the operator 103 to start capturing images, while providing a stop gap before the dictated notes are recorded and allows the operator 103 to minimize any unnecessary recordings.

The recorded images from the image recording system 104 and the dictated notes recorded by the audio recording system 102 can be processed by the control system 108. The control system 108 can be configured to decouple or otherwise separate the recorded audio and the recorded images during processing, while also appropriately associating the recorded audio with images so the data can be temporally aligned or correlated.

The control system 108 can be coupled to the audio recording system 102 and the image recording system 104 and can be configured to translate the spoken audio into text. The control system 108 can also be configured to produce still images from the captured images where video was recorded. The control system 108 can associate the still images and the written text such that the written text is temporally aligned with the still image related to the written text as dictated during the procedure. As a non-limiting example, the control system 108 can utilize a machine learning process to associate related text with related images. In other embodiments, the control system 108 can also label particular procedures, procedural steps, or runs, for example fluoroscopic runs performed by a radiologist, and can further militate against the need for technologist intervention during the procedure.

Advantageously, the system 100 can allow the operator to record dictated notes contemporaneously with the performed procedure. This can allow for more accurate notes while also eliminating additional documentation steps the operator 103 typically performs after the procedure is complete. Advantageously, the documentation system 100 can allow an operator 103 to dictate notes during a medical procedure which can later be coupled and temporally aligned with an image recorded by an image recording system 104. The temporally aligned notes and images can then be used for medical documentation purposed, such as billing.

Figure 4:
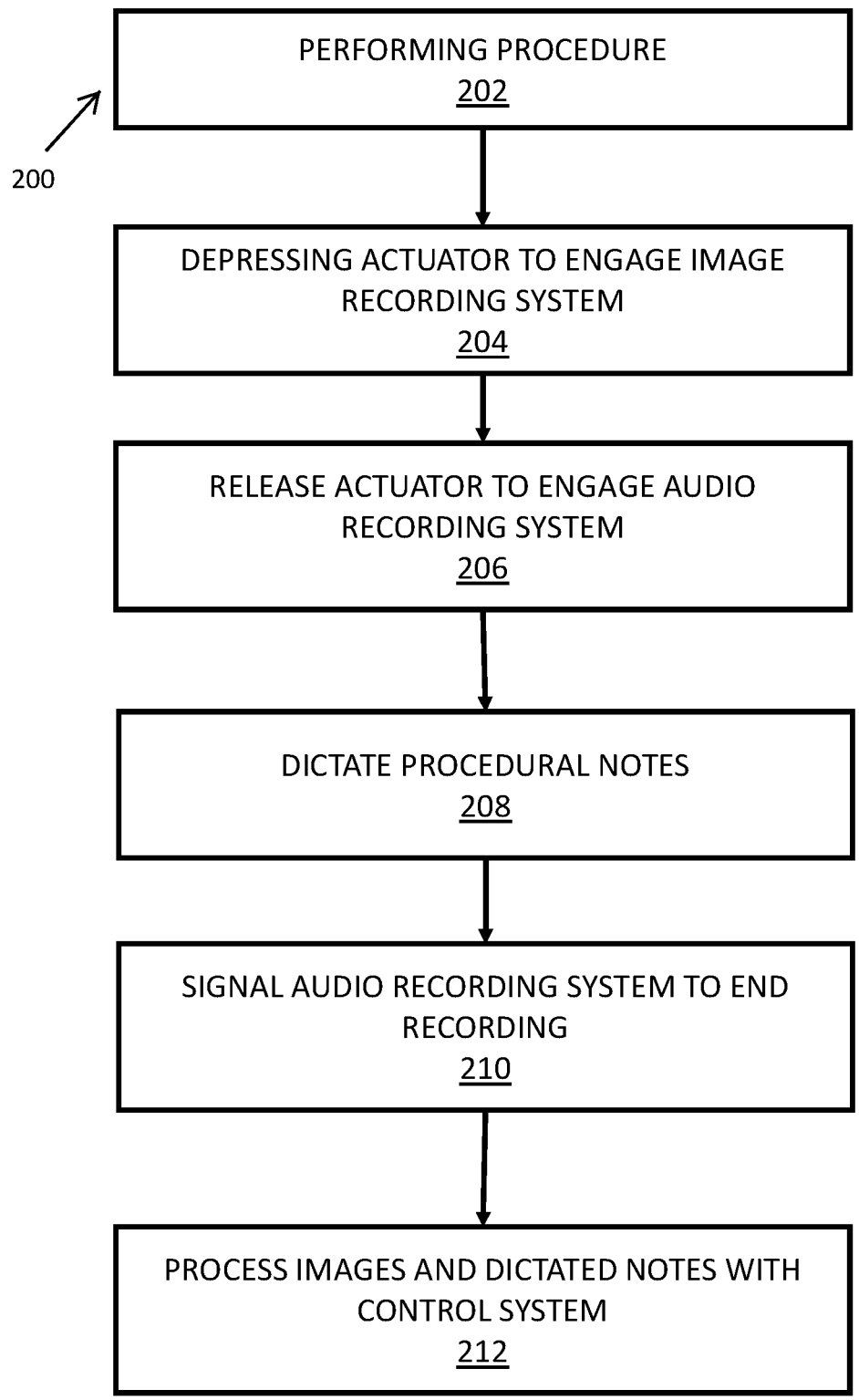
FIG. 4 is a flow diagram illustrating a method for documenting a medical procedure via audio and images.

The present disclosure further contemplates a method 200 for documenting a medical procedure, shown in FIG. 4. In a step 202, a medical documentation system 100 as described herein can be provided. The medical documentation system 100 can include an audio recording system 102, image recording system 104, an actuator 106, and a control system 108. In a step 204, a medical procedure can be performed. In a step 206, the actuator 106 can be depressed to engage the image recording system 104 to create an image. The actuator 106 can be released to engage the audio recording system 102 and to disengage the image recording system 104, in a step 208. In a step 210, the medical procedure information can be dictated to the audio recording system 102 to create procedural notes. The audio recording system 102 can be signaled to end the recording in a step 212. The audio recording system 102 can be signaled by either a spoken word or by an additional further physical actuation. In a step 214, the control system 108 can process and align the image and the procedural notes.

The method can further include a medical documentation system 100 having a third switch 136 configurated configured to simultaneously actuate the audio recording system 102 and the image recording system 104. In a step 216, the third switch 136 can be pushed to simultaneously actuate the audio recording system 102 and the image recording system 104.

The method can also further include a medical documentation system 100 wherein the control system utilizes a machine learning process to associate related audio with a related image. In a step 218, the control system 108 can associate the related audio with the related image using the machine learning process.

Advantageously, the documentation system 100 can allow an operator 103 to dictate notes during a medical procedure which can later be coupled and temporally aligned with an image recorded by an image recording system 104. The temporally aligned notes and images can then be used for medical documentation purposed, such as billing.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, components, and methods can be made within the scope of the present technology, with substantially similar results.

What is claimed is:

1. A method for documenting medical procedure information via audio and images, the method comprising steps of:
providing a medical procedure documentation system including
an audio recording system;
an image recording system;
an actuator configured to actuate each of the audio recording system and the image recording system, wherein the audio recording system is configured to be actuated after the image recording system; and
a control system configured to receive input from each of the audio recording system and the image recording system;
performing a medical procedure;
depressing the actuator to engage the image recording system to create an image;
releasing the actuator to engage the audio recording system;
dictating the medical procedure information to the audio recording system to create a procedural note;
signaling to the audio recording system to end recording; and
processing the image and the procedural note with the control system, wherein the image and the procedural note are aligned.

2. The method for documenting medical procedures of claim 1, wherein the control system is configured to translate the audio from the audio recording system into text.

3. The method for documenting medical procedures of claim 1, wherein the control system utilizes a machine learning process to associate related audio with a related image.

4. The method for documenting medical procedures of claim 1, wherein the control system labels a procedure or a procedural step.

5. The method for documenting medical procedures of claim 1, wherein the audio recording system includes an audio input, a processor, a memory device, and an audio activator.

6. The method for documenting medical procedures of claim 5, wherein the audio input is a clinical documentation client electronic device.

7. The method for documenting medical procedures of claim 6, wherein the clinical documentation client electronic device includes at least one of a lapel microphone, an embedded microphone, and an audio recording device.

8. The method for documenting medical procedures of claim 1, wherein the image recording system includes an image input, a control device, a storage device, and an image activator.

9. The method for documenting medical procedures of claim 8, wherein the image recording system further includes an image output.

10. The method for documenting medical procedures of claim 9, wherein the image output is a monitor configured to display real time images.

11. The method for documenting medical procedures of claim 8, wherein the image input is a video camera configured to capture video and still images.

12. The method for documenting medical procedures of claim 8, wherein the image input is a camera configured to capture still images.

13. The method for documenting medical procedures of claim 1, wherein the actuator includes a first switch configured to actuate the audio recording system and a second switch configured to actuate the image recording system.

14. The method for documenting medical procedures of claim 13, wherein the actuator further includes a third switch configured to simultaneously actuate the audio recording system and the image recording system and further comprising pushing the third switch to simultaneously actuate the audio recording system and the image recording system.

15. The method for documenting medical procedures of claim 1, wherein the control system utilizes a machine learning process to associate related audio with a related image and further comprising associating the related audio with the related image using the machine learning process.

* * * * *